United States Patent
Zoth et al.

(10) Patent No.: US 6,786,873 B2
(45) Date of Patent: Sep. 7, 2004

(54) PORTABLE HANDHELD HEARING SCREENING DEVICE AND METHOD WITH INTERNET ACCESS AND LINK TO HEARING SCREENING DATABASE

(76) Inventors: Peter Zoth, Am Obstgarten 7, D-82205 Gilching (DE); Armin Giebel, Maffeistr. 12, D-82393 Iffeldorf (DE); Franz Fischer, Haidelweg 27, D-81241 Munchen (DE)

(*) Notice: Subject to any disclaimer, the term of this patent is extended or adjusted under 35 U.S.C. 154(b) by 76 days.

(21) Appl. No.: 10/254,294

(22) Filed: Sep. 25, 2002

(65) Prior Publication Data

US 2003/0065252 A1 Apr. 3, 2003

Related U.S. Application Data

(60) Provisional application No. 60/326,628, filed on Oct. 2, 2001, now abandoned.

(51) Int. Cl.[7] ............................. A61B 5/00; A61B 5/12
(52) U.S. Cl. ....................... 600/559; 600/300; 128/920; 73/585
(58) Field of Search ................................. 600/559, 552, 600/300, 301; 128/898, 903, 904, 920; 73/585, 587, 589; 705/4; 709/200, 203, 217

(56) References Cited

U.S. PATENT DOCUMENTS

| | | | | | |
|---|---|---|---|---|---|
| 6,110,126 | A | * | 8/2000 | Zoth et al. | 128/898 |
| 6,231,521 | B1 | * | 5/2001 | Zoth et al. | 73/585 |
| 6,319,207 | B1 | * | 11/2001 | Naidoo | 600/300 |
| 6,379,314 | B1 | * | 4/2002 | Horn | 600/559 |
| 6,428,485 | B1 | * | 8/2002 | Rho | 600/559 |

\* cited by examiner

*Primary Examiner*—Mary Beth Jones
*Assistant Examiner*—Michael Astorino
(74) *Attorney, Agent, or Firm*—Marcus G. Theodore

(57) ABSTRACT

A method and device for audiological screening of infants and newborns by generating one or more stimuli with an audiologic screening device having acoustic transmitters in each ear canal to generate otoacoustic emissions, collecting and transmitting the otoacoustic emissions signals and brain stem response signals, analyzing the same, and transmitting the data to a remote central computer server via a built-in or attached modem or global information network for further analysis and storage.

12 Claims, 4 Drawing Sheets

PORTABLE HANDHELD HEARING SCREENING DEVICE AND METHOD WITH INTERNET ACCESS AND LINK TO HEARING SCREENING DATABASE

RELATED APPLICATIONS

This application is a continuation-in-part application of the Provisional patent application Ser. No. 60/326,628 entitled "Portable Handheld Hearing Screening Device and Method with Internet Access and Link to Hearing Screening Database" filed Oct. 2, 2001, now abandoned.

BACKGROUND OF THE INVENTION

1. Field

This invention pertains to hearing screening devices. In particular, it pertains to a hearing screening device employing handheld detectors of otoacoustic emissions or auditory brainstem responses, which transmit them to a remote central computer server. The remote central computer server analyses the signals and transmits them to an audiologic screen device, which displays the otoacoustic signals responses to determine whether they are or are not significant. These signals can also be analyzed and displayed by the handheld device as well.

2. State of the Art

Hearing Screening, especially on neonates, often takes place in environments, where a personal computer (PC) is not easily available, such as in a maternity clinic, NICU, etc., or, it is conducted by staff who are not very familiar to work with PC-SW. Screening programs should be easy to conduct. They should be able to deliver consistent results independent of the user. It should be a quick operation for personal (doctors, nurses), parents and neonates.

In order to fulfill these requirements, handheld, stand-alone screening devices have been developed. Today, many regional and/or statewide hearing screening programs will be implemented soon within Europe, Japan, USA, and many other countries all over the world.

Hearing screening programs require patient tracking & follow up diagnostic procedures. A screening test will deliver a "Pass"/"Refer" result without indicating in detail the hearing disorder. Therefore, after a "refer" result, a more detailed diagnostic is necessary. This normally is done by an audiologist or an ENT expert using more sophisticated diagnostic equipment. In most cases, these experts and specialized equipment are located in a different clinic or hospital.

Also there is an increasing need for statistical evaluation of the overall screening results requested by the region or the state. Therefore, all results of a screening program need to be transmitted to some central 'Patient Tracking System', which most probably is also located far from the screening location.

Furthermore "quality assurance programs" need to be introduced in order to guarantee that the correct result will be linked to a person. Therefore "safe" data transfer from the single screening device to the central data logging computer (often only one per region) is required.

In order to fulfill these requirements many of the new screening devices can be hooked up to a PC or Laptop, which then transfer the screening results in a second step to the central 'Patient tracking system'. Unfortunately, this approach again requires PC knowledge, which can be avoided by introducing the handheld, stand-alone screening devices. Currently, many handheld hearing screening devices, such as the handheld audiological screening device produced by Fischer-Zoth GmbH under its "echo-screen", trademark, are able to transfer the test result to a local PC or Laptop, either via a cable connection, infrared or other methods, like "blue tooth". The local PC then synchronizes—in a second step—its data with a central "Patient tracking database" located on a remote, central computer. This could be done by sending the data from PC to the central computer via a global communication link, internet, modem connection or other methods. As mentioned, these handheld devices are simple to use, but do not allow the user to enter additional data, transfer the data directly to the "Screening database" or have any direct communication with that database.

To avoid these limitations, a handheld signal transmitting screening device, and receiver associated with a signal analysis database is required to translate the signals and transmit them back to the user. The device and method described below provides such an invention.

SUMMARY OF THE INVENTION

In clinical practice, it is important to transfer the screening results to a tracking system or database quickly and easily. The invention accomplishing these objectives comprises a handheld stand alone screening device and method for using the same, which is adapted to hook up via a modem, network card, bluetooth interface or any other interface with data transmission networks and mediums such as terrestrial and wireless phone networks, optical data transmission networks, local area networks (LAN), wide area networks (WAN). It will communicate directly and autarkic (without means of a PC, Laptop, or personal organizer) with a local or remote server or computer, which handles and memorializes all patient related data. This also allows the access of many screening devices to one local database, either sequentially or contemporaneously.

The device is also capable of receiving the necessary patient data directly from the database stored in the remote or local server. After the local hearing screening measurement has been completed successfully, the device enables a user to dial in directly into the transmission network (terrestrial or wireless phone network) and download the test results into the server. This connection could be done by a dialup connection via a built-in or attached modem (analog, ISDN etc.), via a connection to a local area network (LAN) or wide area network (WAN) or other techiques. The modem connection generally includes the use of mobile phones and the direct access to the internet or intranet. The modem can be any external modem connected to the device or can be built into the device itself.

The objective is to eliminate the use of a local computer and its own operative software for the translating connection. An example of a preferred embodiment of the device and system is that produced by Fischer-Zoth GmbH, which is a handheld OAE and/or ABR Screening device having at least one acoustic transmitter structured for generating one or more stimuli at sound frequencies in each ear canal of an infant, which generate responsive otoacoustic emissions in both ear canals of the infant or newborn. At least one microphone is included and adapted to be removably placed in both ear canals for collecting any transient evoked and distortion product otoacoustic emissions generated by the cochlea in each ear canal in response to the stimulus to generate a frequency mixed product electronic signal. In addition, collection means, such as three electrodes placed onto the scalp, collect any click or frequency stimulated brainstem responses. A digital signal processor is associated with the microphone and electrodes to analyze their electronic signals. It is programmed with statistical processing instructions to statistically evaluate acoustic signal components by means of binomial statistics to determine whether a measured signal contains stimulus elicited components for each frequency on a defined level of significance. An input device is included and associated with the microphones for inputting the frequency mixed product electronic signals and the stimulus frequencies into an incorporated computer processor. The device has an amplifier associated with the computer processor for amplifying the frequency mixed product electronic signals. A frequency analyzer and phase analyzer is associated with the computer processor to analyze a measured acoustic signal and separate the different frequencies and phases from one another. A display for displaying if the otoacoustic signal responses are or are not statistically significant may be included. In addition, a receiver may be included for displaying on the handheld screening device all patient related date, such as the infant patient's name, mother's name, birth date, address, in/outpatient, status, patient identification, hospital identification, patent history, etc. A modem (built-in, external, or plug-in) or external network adapter then transmits the handheld OAE and/or ABR response data, such as environmental noise, probe fit, electrode impedance, signal to noise ratio, etc, to an external database server. An external or internal power source is associated with the computer components, microphones, transmitters, amplifiers, display means, electrodes, modem or external network adapter to operate the same.

The device and system is typically used as described below in the description of the illustrated embodiments.

The invention thus solves the problems with existing handheld systems and provides the following advantages:

No local PC is needed.

No software is to be installed on local computers, therefore no problems are to be expected concerning the operating system requirements No hardware problems are to be expected concerning the ports and other hardware that may vary in local computers.

A data transfer could be initiated at any location where a phone connection, a mobile phone, an LAN socket, a wireless LAN or similar is available from virtually anywhere.

The user only needs to initiate the connection to the central server, the server than can take control and retrieve the measurement data, send patient list data, send messages to the user that are diaplayed directly, synchronize the real time clock, do software upgrades and other functions.

No problems occur regarding which data is on which computer. A central server that is contacted directly (or via any kind of proxy) by the device holds all data. Patient data scurity is managed much easier.

The central server can react on the data that is transferred, for example by sending appropriate messages if a measurement was not performed correctly.

DESCRIPTION OF THE ILLUSTRATED EMBODIMENTS

Figure 1:
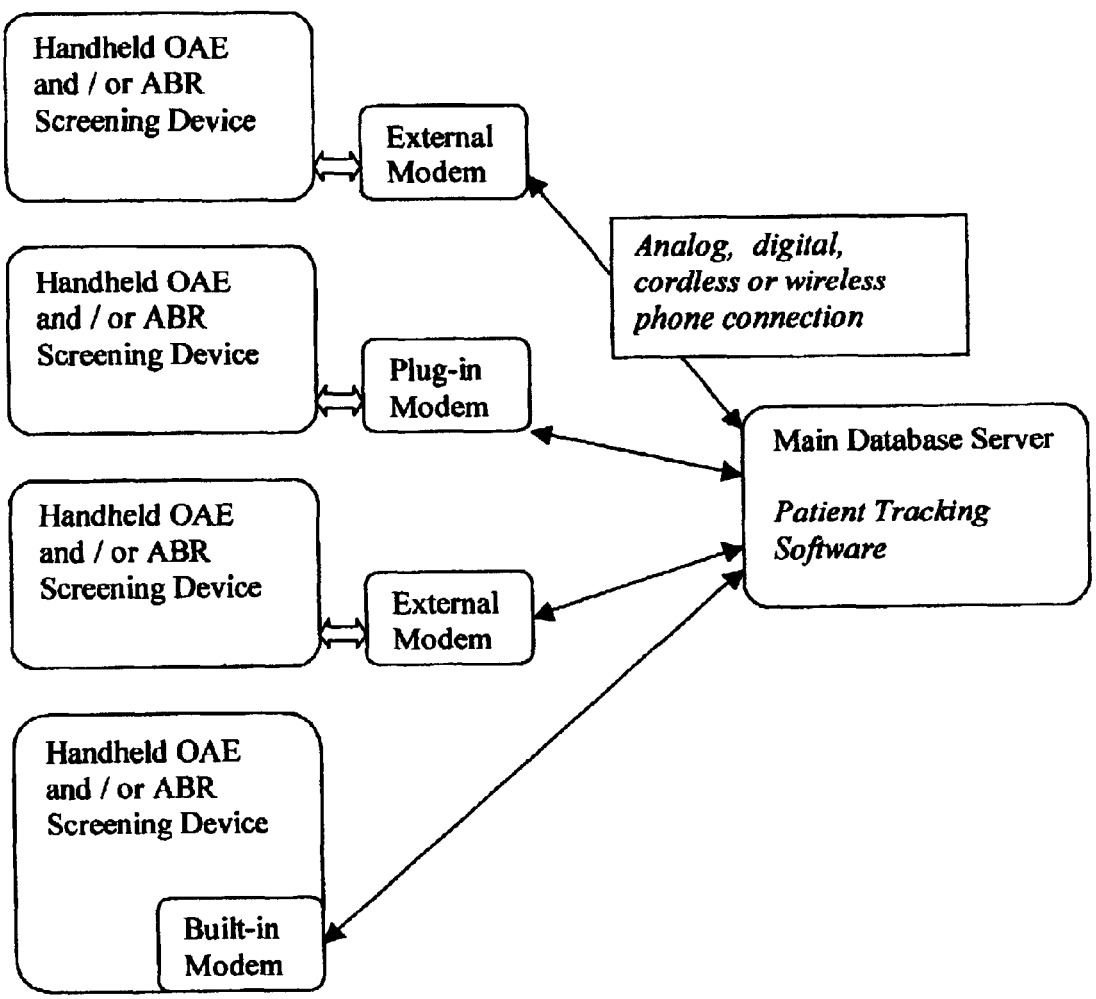
FIG. 1 is a schematic of an embodiment of the invention connected to a central server vial modem.

FIG. 1 illustrates the handheld screening devices connect to a central server via local modems. Four handheld OAE and/or ABR Screening Devices are shown. The first interacts with the main database server via an external modem using analog, digital, cordless or wireless phone connections. The second interacts via a plug-in modem in contact with the main database server. The third interacts via an external modem in contact with the main database server, and the fourth interacts with the main database server via a built-in modem. The screening devices communicate with a central server by actively establishing a dial-up or other connection. The handheld unit is able to store and memorize predefined phone numbers or these phone numbers can be entered via a keyboard similar to a handheld phone. The connection can be established via an analog or digital phone linen, via cordless or cellular phone channels or other media, such as power lines, fiber optic connections, etc. The modem can either be either external with power supplied from the screening device or an independent source, or internal. No local PC is needed. Nor does the user need to use any other device then the screener itself.

Figure 2:
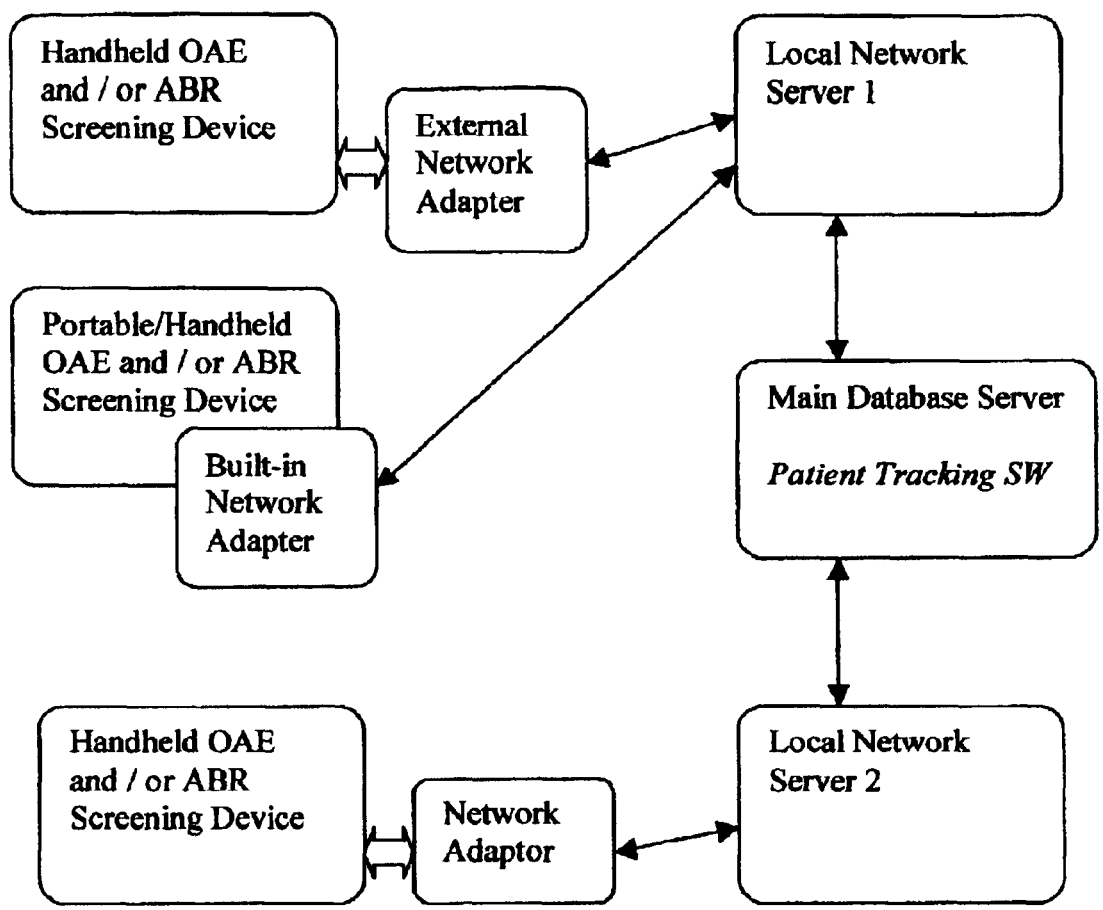
FIG. 2 is a schematic of the embodiment of the invention associated with a server via a local network.

FIG. 2. illustrates how the portable screening devices contact a server via local networks. Three handled OAE and/or ABR Screening Devices are shown. The first is connected via an external network adaptor to a local network server 1 interacting with the main database service. The second has a built-in network adaptor connected to the local network server 1 interacting with the main database server. The third is connected via a network adaptor to a local network server 2 interacting with the main database server. The connection to the server could also be established through a local area network (LAN), which may be Ethernet, 'bluetooth' (wireless standard) or any other local area network. The screening device establishes the connection without the user having to use any software on a local PC. Thus the screening device has a distinct advantage over other screening devices currently available on the market, which need a local PC to transfer data from the device.

Figure 3:
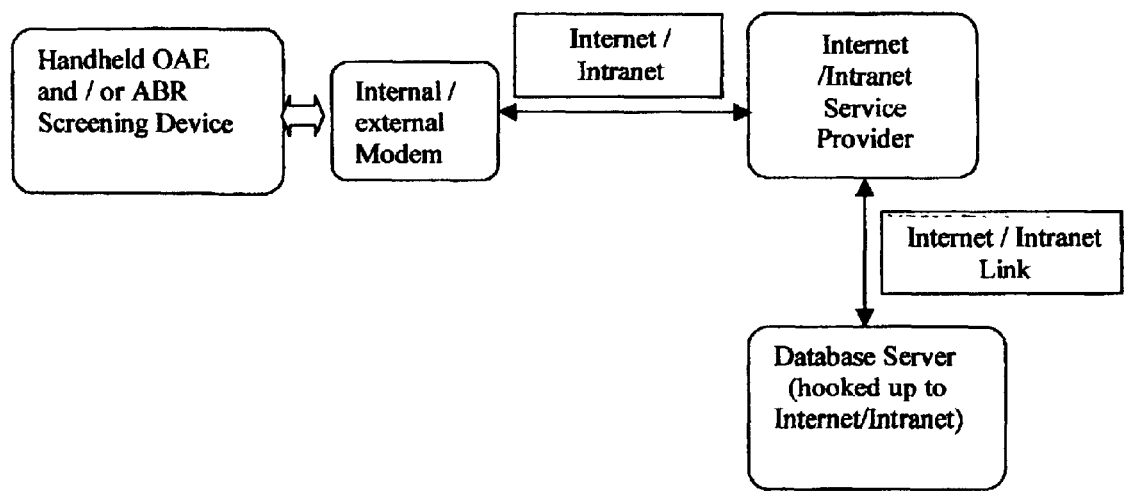
FIG. 3 is a schematic of an embodiment of the invention connected to a main server.

FIG. 3 illustrates how the portable screening devices use global information network (internet)services to connect to the main server. Internet Intranet services can be used in order to connect the screening device to the remote Server. One handheld OAE and/or ABR Screening Device interacts with an internal/external modem connected via an internet/intranet connection to an internet/intranet service provider through an internet/intranet link to a database server. The device can be connected to an Internet service provider via a telephone line or WAP services (wireless application protocol). Measurement data and patient data can be exchanged on a special designed home page.

Figure 4:
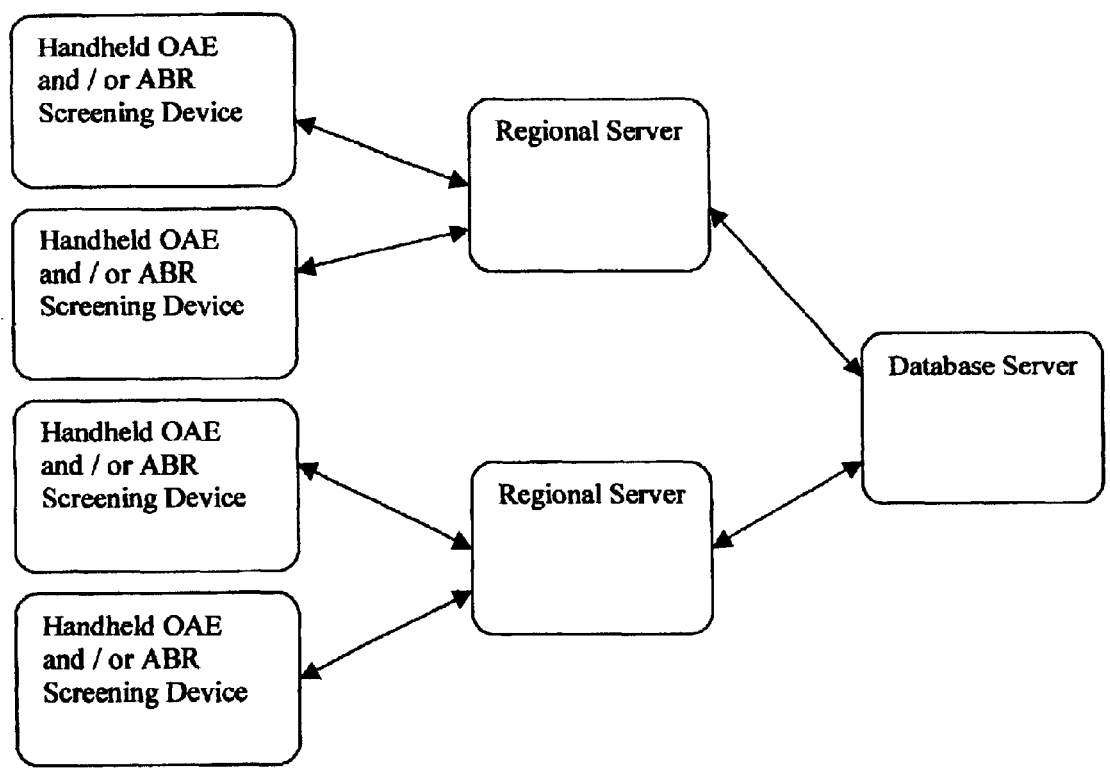
FIG. 4 is a schematic of embodiments of the invention associated with regional servers.

FIG. 4 illustrates the portable screening devices associated with Regional-Servers or WAN-servers used to de-centralize the data management. Four handheld OAE and/or ABR screening devices are shown associated with separate regional servers connected to a database server. Two handheld OAE and/or ABR screening devices are shown connected to one regional server. The second two OAE and/or ABR screening devices are shown connected to a different regional server.

These four figures illustrate a number of different set-ups to operate the handheld screening devices. The server side can be separated into a central server and several 'regional' servers to optimise data handling even in nationwide data management systems. Each regional server is connected to a certain number of devices, which are assigned thereto. The information as to which server to call and how to identify the server can be programmed by the screener. This programming can also be done by the supplier so that the end user does not need to configure anything.

The connection can then also be used for various other actions besides transferring measurement data:

Send patient lists to the screener update or change configuration information on the devices transfer and install new software on the screener setting the real time clock of the screener transferring messages to the user, patient related, device related and service instructions The service-issues messages may be dependent on measurement results. For example, if the refer-rate is too high, the server could recommend a recalibration of the instrument.

Although this specification has made reference to the illustrated embodiments, it is not intended to restrict the scope of the appended claims. The claims themselves recite those features deemed essential to the invention.

We claim:

1. A method for audiological screening of infants and newborns employing a handheld screening device having acoustic transmitters, microphone collection means, scalp electrodes, a digital signal processor, signal transmitters, receivers and a display screen comprising:
    a. generating one or more stimuli with the acoustic transmitters of the handheld screening device in each ear canal of an infant or newborn,
    b. collecting any transient evoked and/or distortion product otoacoustic emission signals generated by the cochlea in each ear canal in response to the stimulus with the microphone collection means placed in the ear, and/or collecting any click or frequency stimulated brainstem response signals by placing electrodes on the scalp,
    c. analyzing the response signals using binomial statistics, different artifact categories by the digital signal processor,
    d. transmitting all results all patient related data and all measurement relevant data from the handheld screening device transmitter to a patient tracking and screening system installed on a remote computer server via transmission means, using an external or built-in modem like interface and a predefined protocol, and
    e. receiving and displaying on the handheld screening device display screen all patient related data directly from a patient tracking system installed on a main server via a link to the server.

2. A method according to claim 1, wherein the means to transmit the frequency mixed product electric signal from the audiologic screening device to a remote computer system comprises dial-up connections using a built-in or attached analog, digital or mobile-phone modem.

3. A method according to claim 1, wherein the means to transmit the frequency mixed product electric signal from the audiologic screening device to a remote computer system comprises LAN connections to transfer and receive data in email-, ftp-, and internet.

4. A method according to claim 1, including sending patient list data and other information from the audiologic screening device to the remote computer server.

5. A method according to claim 3, wherein the patient information includes a list of patients that are to be tested next, along with information on the patients required by the screening program, and other related information including known risk factors or general comments.

6. A method according to claim 1, wherein the audiologic screening device is programmable from the remote computer server.

7. A method according to claim 1, wherein the remote computer server receives and transmits screening and patient data via the patient tracking and screening system, which also controls the handheld screening device procedures with respect to:
    a. setting the real time clock of the screener user,
    b. providing program parameters,
    c. uploading software upgrades to a device,
    d. sending messages to the screener user, including service-issues and procedures.

8. A method according to claim 7, wherein service-issues are dependent on measurement results.

9. A method according to claim 1 including combining an audiologic screening database with other newborn screening data, and using and accessing to a commonly used database on a computer or server which generates and then stores all patient and result data for different screening methods.

10. A device for audiological screening of infants and newborns comprising:
    a. means for generating one or more stimuli with acoustic transmitters in each ear canal of an infant or newborn,
    b. means for collecting any transient evoked and distortion product otoacoustic emissions generated by the cochlea in each ear canal in response to the stimulus with microphone means for generating a frequency mixed product electric signal, and brain stem responses via scalp attached electrodes,
    c. means for analyzing the response signals using binomial statistics, different artifact categories by a digital signal processor associated with the signal collecting means,
    d. means for transmitting the results all patient related data and all measurement relevant data directly from the screening device to a patent tracking system installed on a remote computer server, and
    e. means for receiving and displaying on the handheld screening device display all patient related data directly from a patient tracking system installed on a main server.

11. A device for audiological screening of infants and newborns according to claim 10, wherein the link to the remote server is a modem in communication with the computer server.

12. A device for audiological screening of infants and newborns according to claims 10, including a combined audiologic screening database with other newborn screening data, inputted into the computer server, which generates and stores all patient and result data for different screening methods.

* * * * *